United States Patent
Zander et al.

(10) Patent No.: US 12,108,972 B2
(45) Date of Patent: Oct. 8, 2024

(54) ORTHOPEDIC LOCKING SCREW

(71) Applicant: Stryker European Operations Holdings LLC, Kalamazoo, MI (US)

(72) Inventors: Nils Zander, Eckernförde (DE); Manfred Wieland, Kiel (DE)

(73) Assignee: Stryker European Operations Holdings LLC, Portage, MI (US)

( * ) Notice: Subject to any disclaimer, the term of this patent is extended or adjusted under 35 U.S.C. 154(b) by 433 days.

(21) Appl. No.: 17/378,002

(22) Filed: Jul. 16, 2021

(65) Prior Publication Data
US 2021/0338294 A1   Nov. 4, 2021

Related U.S. Application Data

(63) Continuation of application No. 16/761,117, filed as application No. PCT/IB2017/057688 on Dec. 6, 2017.

(51) Int. Cl.
*A61B 17/86* (2006.01)
*A61B 17/72* (2006.01)
*A61B 17/00* (2006.01)

(52) U.S. Cl.
CPC .......... *A61B 17/863* (2013.01); *A61B 17/725* (2013.01); *A61B 17/8635* (2013.01); *A61B 2017/00526* (2013.01)

(58) Field of Classification Search
CPC ...... A61B 17/80; A61B 17/86; F16B 25/0068
See application file for complete search history.

(56) References Cited

U.S. PATENT DOCUMENTS

| 1,151,861 A | 8/1915 | Brumback |
| 1,756,973 A | 5/1930 | Conner |

(Continued)

FOREIGN PATENT DOCUMENTS

| DE | 29715930 U1 | 10/1997 |
| DE | 102005041586 A1 | 3/2007 |

(Continued)

OTHER PUBLICATIONS

Decision to Grant a European patent for EP17838148.9 dated Apr. 17, 2020; 2 pages.

(Continued)

*Primary Examiner* — David W Bates
(74) *Attorney, Agent, or Firm* — Lerner David LLP

(57) ABSTRACT

An orthopedic locking screw arranged in a bore of an orthopedic implant enables easy removal of a broken locking screw out of the implant. The orthopedic locking screw for a cooperation with a thread in the orthopedic implant comprises a longitudinally extending shaft. The shaft comprises a thread pattern section extending at least partially along the shaft. The thread pattern section comprises a first thread with a first direction, which is a functional thread configured for the cooperation with the thread in the orthopedic implant. The thread pattern section further comprises a second thread with a second direction opposite to the first direction of the first thread. The second thread is superimposed on the first thread and intersects the first thread. An orthopedic locking system comprises the orthopedic locking screw and the orthopedic implant. The locking screw is manufactured by applying the thread pattern section to the longitudinally extending shaft.

20 Claims, 5 Drawing Sheets

(56) References Cited

U.S. PATENT DOCUMENTS

| | | | |
|---|---|---|---|
| 1,933,332 A | 10/1933 | May | |
| 2,183,243 A * | 12/1939 | Meersteiner | F16B 25/0068 411/453 |
| 2,200,227 A | 5/1940 | Olson | |
| 2,232,336 A | 2/1941 | Meersteiner | |
| 2,232,337 A | 2/1941 | Meersteiner | |
| 2,609,604 A | 9/1952 | Sprague | |
| 3,200,691 A | 8/1965 | Neuschotz | |
| 3,426,642 A | 2/1969 | Phipard, Jr. | |
| 3,530,760 A | 9/1970 | Lindstrand | |
| 3,643,722 A | 2/1972 | Oestereicher | |
| 4,259,889 A * | 4/1981 | Capuano | F16B 25/0057 411/386 |
| 4,406,623 A | 9/1983 | Grafelmann et al. | |
| 4,479,748 A | 10/1984 | Uhlmann | |
| 4,546,639 A | 10/1985 | Corrette | |
| 4,652,194 A | 3/1987 | Tajima et al. | |
| 4,806,054 A | 2/1989 | Rath | |
| 4,842,467 A * | 6/1989 | Armstrong | F16B 35/048 411/386 |
| 5,094,618 A | 3/1992 | Sullivan | |
| 5,110,245 A * | 5/1992 | Hiroyuki | F16B 25/0047 411/417 |
| 5,340,254 A | 8/1994 | Hertel et al. | |
| 5,425,407 A | 6/1995 | Archuleta et al. | |
| 5,702,443 A | 12/1997 | Brånemark | |
| 5,702,445 A | 12/1997 | Brånemark | |
| 5,941,911 A | 8/1999 | Buechel | |
| 6,347,917 B1 | 2/2002 | Kato | |
| 6,672,813 B1 | 1/2004 | Kajita et al. | |
| 6,979,163 B2 | 12/2005 | Brletich et al. | |
| 7,156,600 B2 | 1/2007 | Panasik et al. | |
| 7,163,366 B2 | 1/2007 | Chen | |
| 7,217,195 B2 | 5/2007 | Matsubayashi | |
| 7,832,971 B2 | 11/2010 | Mair | |
| 7,862,279 B2 | 1/2011 | Stiebitz et al. | |
| 7,862,280 B2 | 1/2011 | Su | |
| 7,955,364 B2 | 6/2011 | Ziolo et al. | |
| 7,988,396 B2 | 8/2011 | Weiss et al. | |
| 8,221,119 B1 | 7/2012 | Valen | |
| 8,322,960 B2 | 12/2012 | Gong et al. | |
| 8,323,321 B2 | 12/2012 | Gradl | |
| 8,337,535 B2 | 12/2012 | White et al. | |
| 8,348,576 B1 | 1/2013 | Gaw | |
| 8,408,855 B2 | 4/2013 | Stiebitz et al. | |
| 8,480,342 B2 | 7/2013 | Stiebitz et al. | |
| 8,518,090 B2 | 8/2013 | Huebner et al. | |
| 8,858,142 B2 | 10/2014 | Suzuki et al. | |
| 8,870,931 B2 | 10/2014 | Dahners et al. | |
| 8,985,926 B2 | 3/2015 | Hamano et al. | |
| 9,078,714 B2 | 7/2015 | Allinniemi et al. | |
| 9,265,542 B2 | 2/2016 | Koay et al. | |
| 9,314,286 B2 | 4/2016 | Bottlang et al. | |
| 9,322,422 B2 | 4/2016 | Park | |
| 9,387,022 B2 * | 7/2016 | Koay | A61B 17/866 |
| 9,433,454 B2 | 9/2016 | Paolino et al. | |
| 9,532,822 B2 | 1/2017 | Fang et al. | |
| 9,636,158 B2 | 5/2017 | Fang et al. | |
| 9,707,059 B2 | 7/2017 | Giorno | |
| 9,719,545 B2 | 8/2017 | Hsu | |
| 9,822,810 B2 | 11/2017 | Su et al. | |
| 9,848,927 B2 | 12/2017 | Giorno | |
| 9,903,405 B2 | 2/2018 | Fujimoto et al. | |
| 9,918,764 B2 | 3/2018 | Huwais | |
| 10,179,014 B1 | 1/2019 | Menmuir et al. | |
| 10,383,668 B2 | 8/2019 | Rutledge et al. | |
| 10,624,686 B2 | 4/2020 | Lopez et al. | |
| 10,772,665 B2 | 9/2020 | Bosshard et al. | |
| 10,816,027 B2 | 10/2020 | May | |
| 2003/0108403 A1 | 6/2003 | Scoyoc | |
| 2004/0073218 A1 | 4/2004 | Dahners | |
| 2004/0223830 A1 | 11/2004 | Panasik et al. | |
| 2005/0165400 A1 | 7/2005 | Fernandez | |
| 2006/0285940 A1 * | 12/2006 | Walther | F16B 25/0068 411/421 |
| 2007/0043366 A1 | 2/2007 | Pfefferle et al. | |
| 2007/0071576 A1 | 3/2007 | Romano et al. | |
| 2007/0269288 A1 | 11/2007 | Palm | |
| 2008/0118330 A1 | 5/2008 | Stiebitz et al. | |
| 2008/0118893 A1 | 5/2008 | Armellini et al. | |
| 2008/0286072 A1 | 11/2008 | Stiebitz et al. | |
| 2009/0003966 A1 * | 1/2009 | Hsu | F16B 15/06 411/394 |
| 2010/0240010 A1 | 9/2010 | Holmstrom | |
| 2011/0097178 A1 | 4/2011 | Stiebitz et al. | |
| 2011/0195380 A1 | 8/2011 | Giorno | |
| 2011/0262245 A1 | 10/2011 | Michiwaki | |
| 2012/0290017 A1 * | 11/2012 | Haidukewych | A61B 17/82 606/324 |
| 2014/0017035 A1 | 1/2014 | Michiwaki | |
| 2014/0214034 A1 | 7/2014 | Rayes et al. | |
| 2014/0236242 A1 | 8/2014 | Robinson | |
| 2014/0277139 A1 | 9/2014 | Vrionis et al. | |
| 2014/0329202 A1 | 11/2014 | Zadeh | |
| 2015/0272646 A1 * | 10/2015 | Russell | A61B 17/8841 606/93 |
| 2015/0297275 A1 | 10/2015 | Huwais | |
| 2015/0308487 A1 | 10/2015 | Michiwaki | |
| 2015/0337885 A1 | 11/2015 | Whitlock et al. | |
| 2017/0071703 A1 | 3/2017 | Hall et al. | |
| 2017/0343029 A1 | 11/2017 | Hsu | |
| 2018/0092751 A1 | 4/2018 | Vrionis et al. | |
| 2019/0343565 A1 | 11/2019 | Tempco et al. | |

FOREIGN PATENT DOCUMENTS

| | | |
|---|---|---|
| DE | 102006057259 A1 | 5/2008 |
| DE | 102007024240 A1 | 11/2008 |
| DE | 202011000982 U1 | 10/2011 |
| EP | 1864616 A1 | 12/2007 |
| EP | 1925828 A2 | 5/2008 |
| EP | 2012026 A2 | 1/2009 |
| EP | 2210568 A1 | 7/2010 |
| EP | 2256371 A1 | 12/2010 |
| EP | 3040582 A1 | 7/2016 |
| EP | 3225858 A1 | 10/2017 |
| FR | 2500090 A1 | 8/1982 |
| GB | 2106023 A | 4/1983 |
| JP | 2016515857 A | 6/2016 |
| WO | 0212736 A1 | 2/2002 |
| WO | 2010088213 A2 | 8/2010 |
| WO | 2014093487 A1 | 6/2014 |
| WO | 2014149746 A1 | 9/2014 |
| WO | 2014165194 A1 | 10/2014 |
| WO | 2015132331 A1 | 9/2015 |
| WO | 2017086953 A1 | 5/2017 |
| WO | 2017136801 A1 | 8/2017 |

OTHER PUBLICATIONS

Intent To Grant European Patent Application No. 17838148.9 dated Dec. 12, 2019; 42 pages.

International Search report for or PCT/IB2017/057688 mailed Feb. 14, 2019; 6 pages.

MakerBot Thingiverse, Magic Screw for Makerbot, 2011. Note the youtube video linked in the summary seciton on this bage to see functionality. https://www.thingiverse.com/thing: 13893 Accessed Mar. 5, 2021 (Year: 2011).

Notice to Pay fees & Partial International Search Report including Provisional Opinion for PCT/IB2017/057688 dated Aug. 21, 2018; 9 pages.

Written Opinion of the International Searching Authority for PCT/IB2017/057688 mailed Feb. 11, 2019; 13 pages.

* cited by examiner

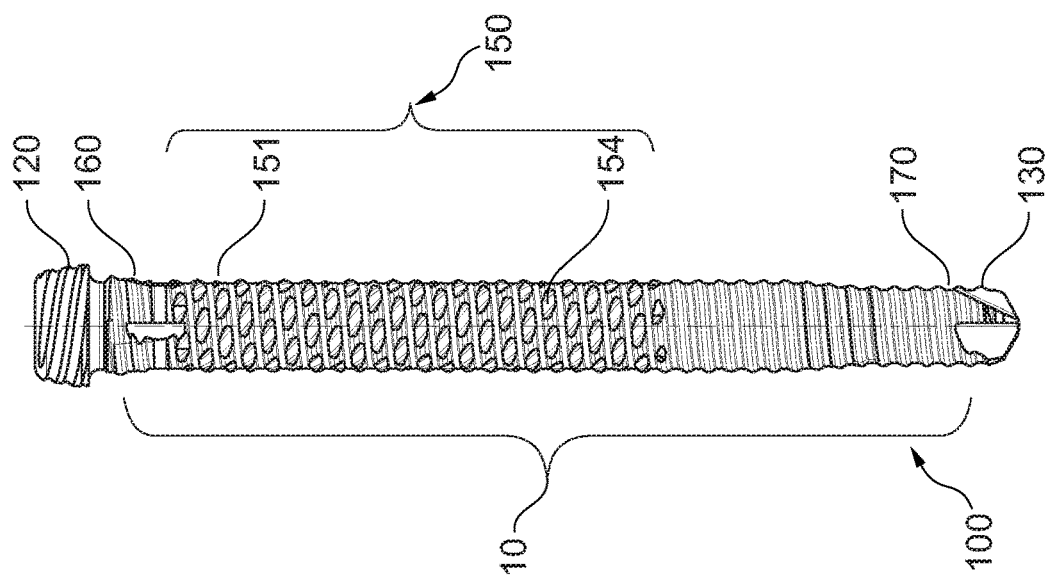
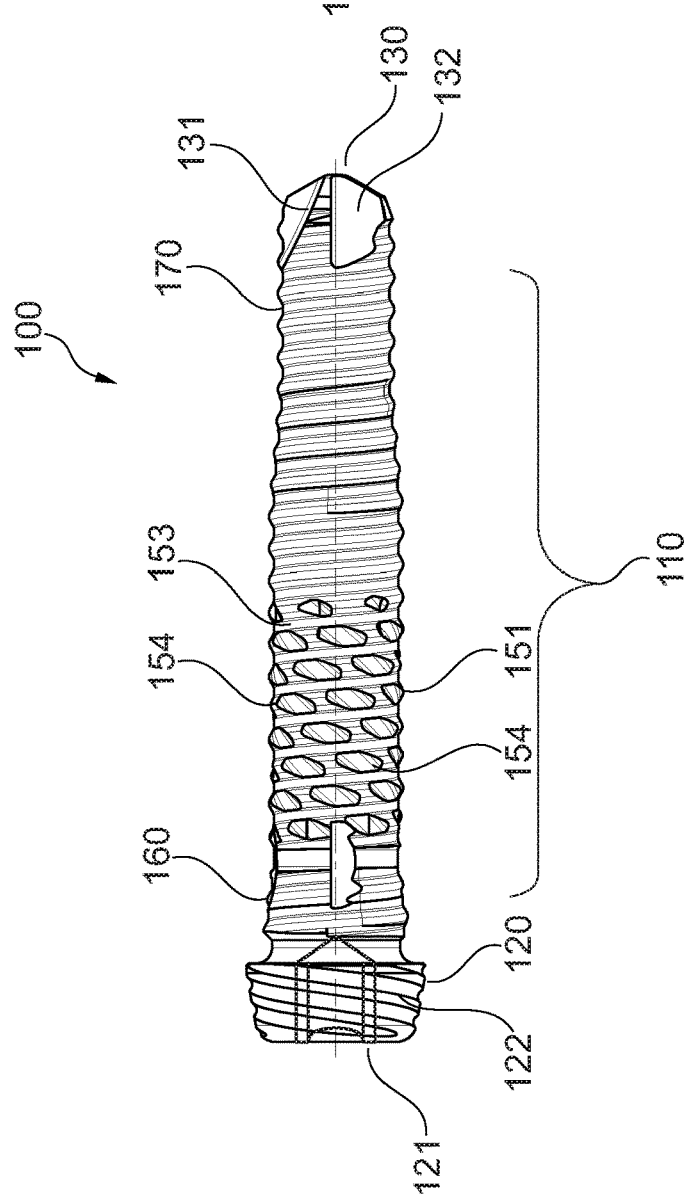

ORTHOPEDIC LOCKING SCREW

CROSS-REFERENCE TO RELATED APPLICATIONS

The present application is a continuation of U.S. patent application Ser. No. 16/761,117, filed on May 1, 2020, which is a U.S. national phase entry under 35 U.S.C. § 371 of International Application No. PCT/IB2017/057688, filed on Dec. 6, 2017, the disclosures of which are hereby incorporated by reference herein in their entirety.

FIELD OF INVENTION

The invention relates to an advanced orthopedic locking screw configured to be arranged in a bore of an orthopedic implant, an orthopedic locking system comprising such locking screw and a method for manufacturing such orthopedic locking screw. Particularly, the invention allows a removal of a broken locking screw out of an implant.

BACKGROUND OF THE INVENTION

In orthopedic procedures, it is often necessary to secure an orthopedic implant. In such cases, an orthopedic locking screw of an orthopedic fastening system is often used to secure the orthopedic implant to a bone or to another orthopedic implant. The screw sometimes breaks during installation or use so that a part of the screw remains in a hole into which it was threaded. In some instances, the locking screw may be broken due to excessive loading or accidents, e.g., due to shearing forces, at the fixation interface. Usually, a broken or damaged locking screw needs to be removed from the human body.

Various devices exist to remove such implanted broken screws. Some of these prior art devices have their own screw threads to be attached to the broken screw for reverse turning of the screw for its removal. Those instruments often have a tapered opening at their threads for telescoping with the broken screw to grip it in the removal process. Such devices have the disadvantage of also removing a relatively large core of the bone, resulting in considerable bone loss. Accordingly, there is a need to provide a locking screw, which when broken, can be easily removed essentially without damaging bone tissue.

BRIEF SUMMARY OF THE INVENTION

The problems of the prior art are addressed by the subject matter of the independent claims, wherein further embodiments are incorporated in the dependent claims. Aspects of the invention described in the following apply also to the advanced orthopedic locking screw system and the method for manufacturing the orthopedic locking screw.

According to an aspect of the present invention, an orthopedic locking screw is presented. The orthopedic locking screw is configured for a cooperation with a thread in an orthopedic implant and comprises a longitudinally extending shaft. The longitudinally extending shaft comprises a thread pattern section extending at least partially along the shaft. The thread pattern section comprises a first thread with a first direction, in which the first thread is a functional thread configured for the cooperation with the thread in the orthopedic implant. The thread pattern section further comprises a second thread with a second direction opposite to the first direction the first thread. The second thread is superimposed on the first thread and intersects the first thread.

The orthopedic locking screw may be an angular stable locking screw and may be provided to secure the orthopedic implant. The orthopedic locking screw may fasten the orthopedic implant precisely without additional components through a bore of the implant. The bore may be arranged with an internal thread to cooperate with the thread pattern section of the locking screw.

The functional thread of the locking screw may interact with the internal thread of the orthopedic implant. However, when the locking screw fatigues, it usually bends and breaks within the implant itself. The functional thread of the thread pattern section may then also allow for removal of a retained portion of the screw without damaging the adjacent bone tissue. In other words, the thread pattern section may allow an interaction between the thread turns of the functional thread of the locking screw and the internal thread of the orthopedic implant and, at the same time, allow for an easily removal of the retained broken screw from the implant in case of a failure of the screw.

The first thread of the thread pattern section might be screwed in the bore of the implant to fasten it. The second thread of the thread pattern section might be a counter screw thread in opposite direction to the first thread such that the second thread and the first thread intersect each other in the thread pattern section. The term "intersect" means that second thread turns overlap first thread turns and vice versa. Accordingly, each thread intervenes, interrupts and/or interferes a counter thread flow. Accordingly, the second thread turns interrupt the first thread flow and vice versa. In other words, the first thread turns are cut by the passing second thread turns and vice versa. The first and second threads may thereby form at least one island, and preferably a plurality of intersection islands, along the circumference of the thread pattern section. Each intersection island may resemble a roller of a music box. The thread pattern section can also be understood as a groove and intersection island system.

In an example, the thread pattern section may comprise essentially rhombic protrusions and multiple grooves between the rhombic protrusions. By intersecting the first thread and second thread, crossing crests of the first and second threads and crossing roots of the first and second threads may form grooves. If crossing crests of the first thread meet crossing roots of the second thread or crossing roots of the first thread meet crossing crests of the second thread, an intersecting area may form a rhombic protrusion due to a helical structure of the threads. Accordingly, a strong internal cooperation of the first thread of the locking screw and the internal thread of the implant can be realized. At the same time, the thread pattern section may be efficiently sheared off when removing the broken locking screw.

In an example, the functional first thread and the superimposed second thread of the thread pattern section may have the same pitch. Hence, grooves and rhombic protrusions in the thread pattern section may have identical size and shape, which allows an even distribution of the interlocking and shearing-off forces between the first thread of the locking screw and the internal thread of the implant. In another example, the functional first thread and the superimposed second thread of the thread pattern section may have a different pitch.

In an example, the functional thread may be a right hand thread and the superimposed second thread may be a left hand thread. In another example, the functional thread is a left hand thread and the second thread is a right hand thread. Usually the locking screw is turned in the right hand direction when fastened. Hence, any special skills may not be required to operate or even to manufacture the functional thread section of the locking screw.

In an example, the orthopedic locking screw may further comprise a neck thread arranged between the thread pattern section and a screw head of the locking screw. The neck thread may have an identical pitch and direction as the functional first thread. Hence, the neck thread and the functional thread can be continuously formed on the shaft of the locking screw. In another example, the neck thread may have a different pitch and direction as the functional first thread.

In an example, a cross section of the thread pattern section of the orthopedic locking screw within a plane along a central axis defined by the screw may have an initial major diameter. Further, a screw neck area near a screw head may have a neck major diameter, and the neck major diameter may be larger than the initial major diameter. The major diameter of the thread is to be understood as the larger of two extreme diameters delimiting the height of the thread profile, as a cross-sectional view is taken in a plane containing the axis of the threads. For a screw, this is generally its outside diameter. Hence, the neck thread may serve to interlock the locking screw in a cortex of a bone, when the locking screw is fastened in the bone or to the implant. The major diameter from the neck thread to the thread pattern section may be reduced steadily along the longitudinal direction of the shaft or stepwise between the screw head and the thread pattern section.

In an example, the orthopedic locking screw further comprises a tip thread arranged between the thread pattern section and a screw tip. The tip thread may have an identical pitch and direction as the functional first thread. Hence, the tip thread and the functional thread can be continuously formed on the shaft of the locking screw. In another example, the tip thread may have a different pitch and direction as the functional first thread.

As stated above, a cross section of the thread pattern section of the orthopedic locking screw may have an initial major diameter. A screw tip area near the screw tip may have a tip major diameter and the tip major diameter may be smaller than the initial major diameter. Accordingly, the locking screw passing the implant also can be fastened on the opposite side to an insertion location of the locking screw in the bone. The major diameter from the thread pattern section to the tip thread may be reduced steadily along the longitudinal direction of the shaft or stepwise between the thread pattern section and the screw tip.

In an example, the orthopedic locking screw may further comprise a screw head having a (counter) screw thread. The (counter) screw thread may have a direction similar or opposite to the functional thread. In the latter case, the orthopedic locking screw can be held by a screw driver engaged with, and preferably threaded onto, the counter screw thread. The counter screw thread may be arranged outwardly on the screw head in an opposite direction to the fastening direction of the locking screw. For example, when the locking screw is fastened in the orthopedic implant in the right hand direction, the locking screw may be firmly held to the screw driver, because the screw head is screwed in a left hand direction into the screw driver. As a result, it may not be necessary to hold the screw with a second hand.

In an example, the second thread intersecting the functional first thread may configure thread turns of the functional first thread for an override of the normal operation of the first thread when forcefully removing the screw out of the implant. The functional thread of the thread pattern section configured for an override of its thread turns may allow for removal of a retained portion of the screw without damaging the adjacent bone tissue. In other words, the locking screw may interact with the internal thread of the orthopedic implant by means of its functional thread configured for an override of its thread turns. The term "configured for an override" may be understood in that the thread turns of the functional thread of the locking screw may be reduced to allow a shearing off and thereby a striking or hammering of the screw throughout the implant to remove the locking screw when it is broken. A residual shear surface of the thread turns may be still sufficient to allow an interaction between the thread turns of the functional thread of the locking screw and the internal thread of the orthopedic implant.

In an example, the second thread intersecting the functional first thread may configure a shearing area of the thread turns of the functional first thread for an intended shearing-off when forcefully removing the orthopedic locking screw in case of a failure of the locking screw. The shearing area may be arranged on a proximal portion of the shaft of the locking screw, may extend in a longitudinal direction of the screw and may serve as a main contact surface of the locking screw to interlock with the internal thread in the bore of the orthopedic implant. As a result, the shearing area of the functional thread allows a locking in the bore of the implant between the internal thread of the implant and the functional thread of the screw and to be easily sheared off in case the broken locking screw has to be extracted.

In an example, the orthopedic implant is an intramedullary nail and the functional thread of the thread pattern section is configured for a cooperation with an inner thread of a bore of the intramedullary nail. Since a breakage of the orthopedic locking screw often occurs in such an intramedullary nail, it is in this case particularly advantageous if the screw can be easily removed.

In an example, the shaft of the orthopedic locking screw may comprise a cannulation.

According to the present invention, also an orthopedic locking system is presented. The orthopedic locking system comprises above described orthopedic locking screw and an orthopedic implant. The orthopedic locking screw is configured for a cooperation with a thread in the orthopedic implant. The orthopedic locking screw may allow a stable transverse locking at a distal end of the orthopedic implant.

According to another aspect of the present invention, a manufacturing method for an orthopedic locking screw is presented. It comprises the following steps:
applying a first thread of a thread pattern section onto a longitudinally extending shaft with a first direction, the first thread being a functional thread configured for the cooperation with the thread of the orthopedic implant, and
applying a second thread of the thread pattern section onto the longitudinally extending shaft with a second direction opposite to the first direction of the first thread. The second thread is superimposed on the first thread and at least partially intersects the first thread.

The thread pattern section may comprise grooves between essentially rhombic protrusions. The functional first thread and the superimposed second thread of the thread pattern section may have the same pitch. The functional thread may be a right hand thread.

It shall be understood that the orthopedic locking screw and the orthopedic locking system according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

FIG. 2a and FIG. 2b are side views of orthopedic locking screws according to embodiments of the present invention.

DETAILED DESCRIPTION

In orthopedic procedures, it is often necessary to secure an orthopedic implant. In such cases, an orthopedic fastening system may be provided in which an orthopedic locking screw secures an orthopedic implant to a bone or to another orthopedic implant.

Figure 1:
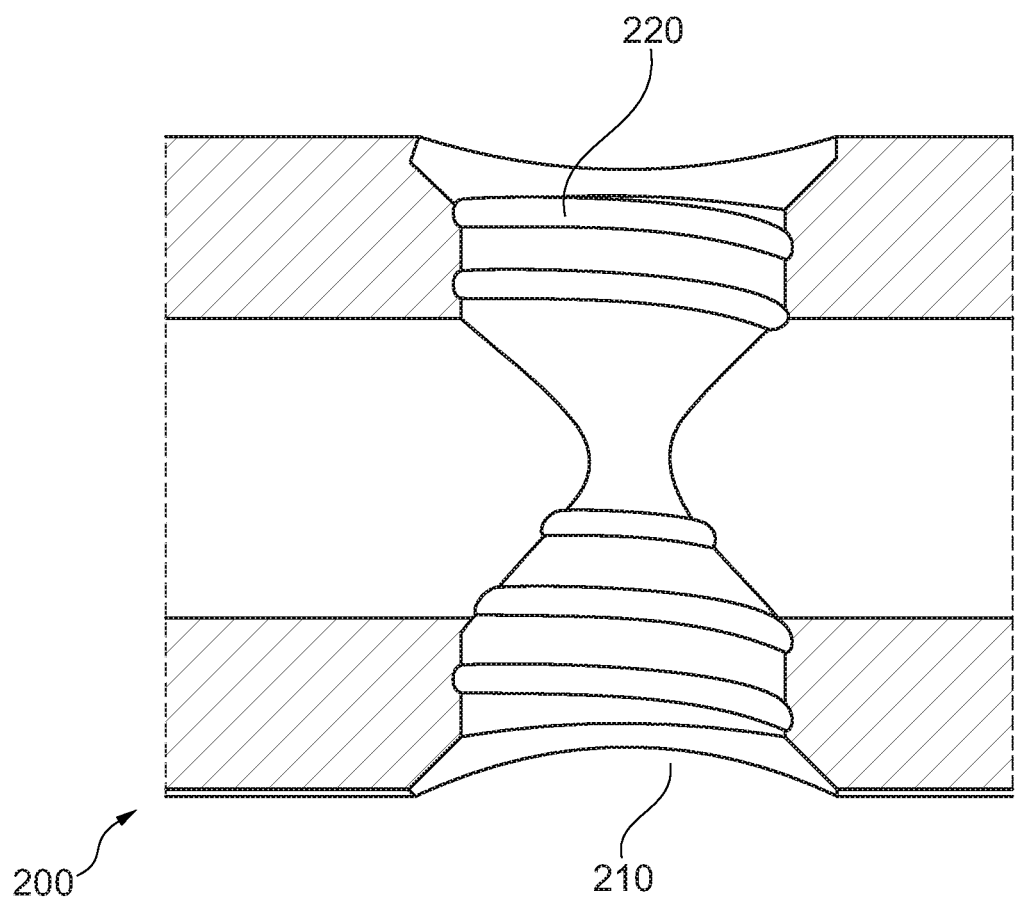
FIG. 1 is a side cross-sectional view of an orthopedic implant.

As shown in FIG. 1, an orthopedic implant 200 generally comprises at least a bore 210 and an internal thread 220 to secure a locking screw (not shown). In some arrangements, the orthopedic implant may be, for example, an intramedullary bone nail, with one or more bores extending partially or completely therethrough for receiving a locking screw therein. The orthopedic implant is not limited to being an intramedullary bone nail. The orthopedic implant may be, for example, a plate or bone connector, or another type of orthopedic implant.

FIGS. 2a and 2b illustrate an orthopedic locking screw 100 according to an embodiment of the present invention. The orthopedic locking screw 100 comprises a shank or shaft 110, a screw head 120 and a screw tip 130. The shaft 110 may have an elongate, form. The shaft 110 may be generally cylindrical, having a substantially constant major diameter extending between the screw head 120 and the screw tip 130. The locking screw 100 may have a region of smaller and tapering diameter at the end near the screw tip.

The screw head 120 at a proximal end of the locking screw 100 comprises a recess 121 and an outer thread 122. The recess 121 is configured to receive a rotational drive, such as a screw driver or wrench. Hence, the orthopedic locking screw 100 may be rotated around a longitudinal axis of the shaft 110 in order to operably engage the orthopedic locking screw 100 with bone 300 (see FIG. 4a) and/or the implant 200. The recess 121 is not limited to a particular shape. For example, the recess 121 may have a socket adapted to receive a square or hexagonal drive, or a slot for receiving a screw driver. The outer thread 122 of the screw head 120 is configured in an opposite direction to the fastening direction of the locking screw 100 to be held by the screw driver by means of a self-holding mechanism during threading of the locking screw 100 into a mating structure, such as the orthopedic implant 200.

The screw tip 130 extends from the distal end of the shaft 110. The screw tip 130 tapers to a point or, alternatively, to a blunt nose, such as a rounded, flat, or truncated nose. The tip 130 may comprise a self-tapping element 131 for tapping a bore into bone 300. The self-tapping element 131 may comprise at least one, and optionally two or more diametrically opposite axial grooves 132 extending along the tip 130. The axial grooves 132 may be at least partially helical. The axial grooves 132 define an edge that may act to scoop away bone or other material as the orthopedic locking screw 100 is rotated and advanced into the bone 300.

The orthopedic locking screw 100 may be more particularly detailed by a thread pattern section 150, a neck 160 between the head 120 and the thread pattern section 150, and a transition section between the thread pattern section 150 and the tip 130. As shown in FIG. 2a, the head 120 of the locking screw 100 may be configured to have a bigger major diameter than a major diameter of the shaft 110. Further, in one arrangement, one or both of a major diameter of the neck 160 and a major diameter of the transition section 170 may be similar to the major diameter of the thread pattern section 150. In the present embodiment, the major diameter of the neck 160 is larger than the major diameter of the thread pattern section 150, and a major diameter of the tip 130 is smaller than the major diameter of the thread pattern section 150. Hence, the transition section 170 is provided with a taper from the thread pattern section 150 to the distal end of the locking screw, i.e. the tip 130. In this manner, the transition section 170 is used to draw the shaft 110 through the implant bore 220.

Figure 3A:
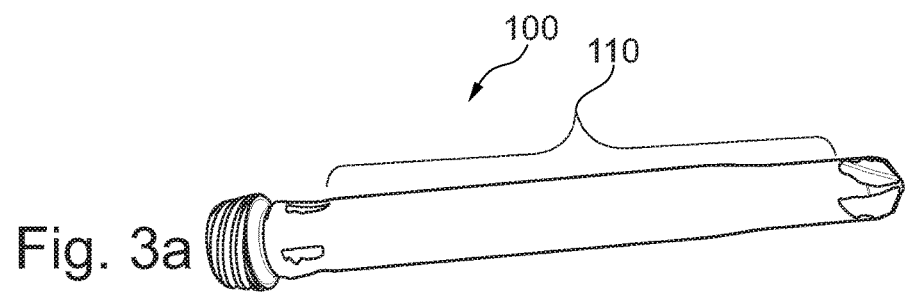
FIG. 3a is a perspective view of an orthopedic locking screw before forming a thread.
Figure 3B:
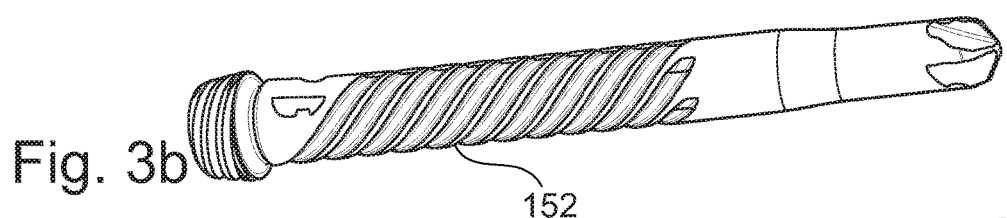
FIG. 3b is a perspective view of the orthopedic locking screw of FIG. 3a with a left hand thread.
Figure 3C:
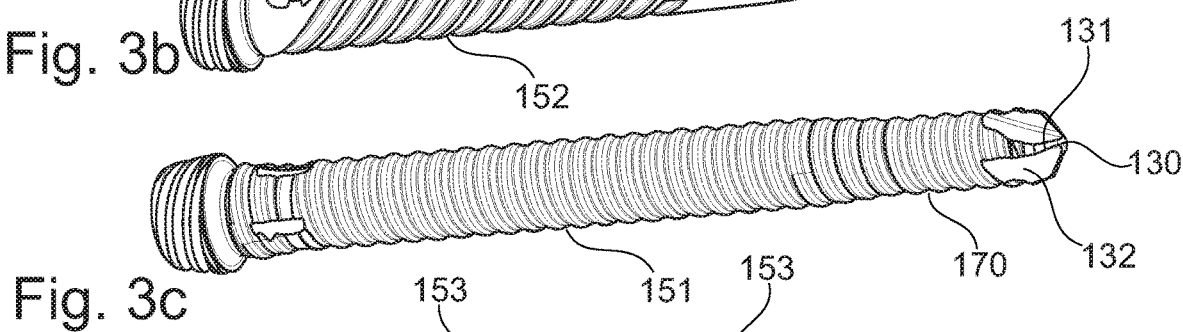
FIG. 3c is a perspective view of the orthopedic locking screw of FIG. 3a with a right hand thread.
Figure 3D:
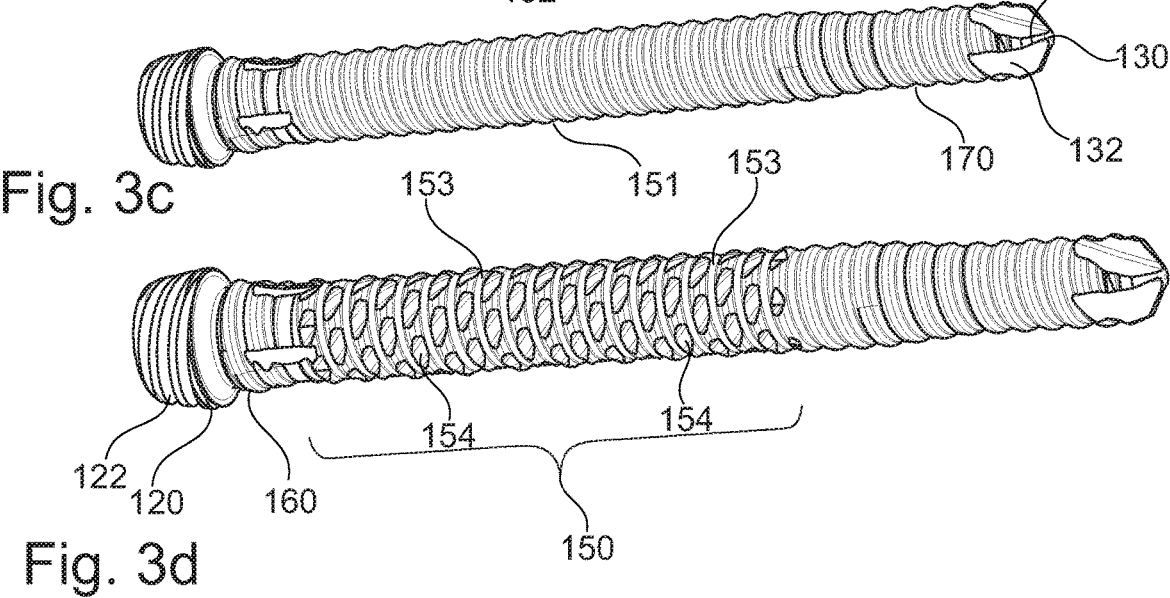
FIG. 3d is a perspective view of the orthopedic locking screw of FIG. 3a after applying left and right hand threads.

FIG. 3a to FIG. 3d show an exemplary manufacturing method of the locking screw according to an embodiment of the present invention. As a first step to shape the thread pattern section 150 of the locking screw 100, a left hand thread 152 is arranged in the thread pattern section 150, as shown by a comparison of FIG. 3a and FIG. 3b. Afterwards, a right hand thread 151 is arranged at least partially, and preferably completely, from the neck 160 to the distal end of the locking screw 100 (comparison between FIG. 3a and FIG. 3c). Accordingly, the neck portion 160, the transition portion 170 and the tip portion 130 are threaded in the same direction and with the same pitch as the thread pattern section 150. The right hand thread serves as a functional thread 151 (i.e., a helically extending crest) configured to cooperate with an internal thread, such as the inner thread 220 of the orthopedic implant 200. Since the left hand thread and the right hand thread intersect each other in the thread pattern section 150, the thread pattern section 150 is constituted of remaining flanks of both threads and grooves 153 (i.e., helically extending roots) between the flanks accordingly. In this respect, there may be a step 155 between a base of the grooves 153 and the flanks. As shown by FIG. 3b and FIG. 3c, the pitch of the left hand thread is larger than the pitch of the right hand thread.

The remaining flanks in the thread pattern section 150 are provided in the form of rhombic protrusions 154. In some embodiments, and as shown in FIG. 4c, the thread pattern section 150 is formed such that at least some of the rhombic protrusions 154 include a circumferentially planar surface in between a leading edge 156 and a trailing edge 157 within the rhombic protrusion 154. The thread turns of the functional thread 151 in the thread pattern section 150 include a shearing area provided by the rhombic protrusions 154. The thread pattern section 150 is configured for the cooperation with the inner thread 220 of the orthopedic implant 200 and for an intended shearing-off when removing the orthopedic locking screw 100 in a case of a failure of the screw 100.

Figure 4B:
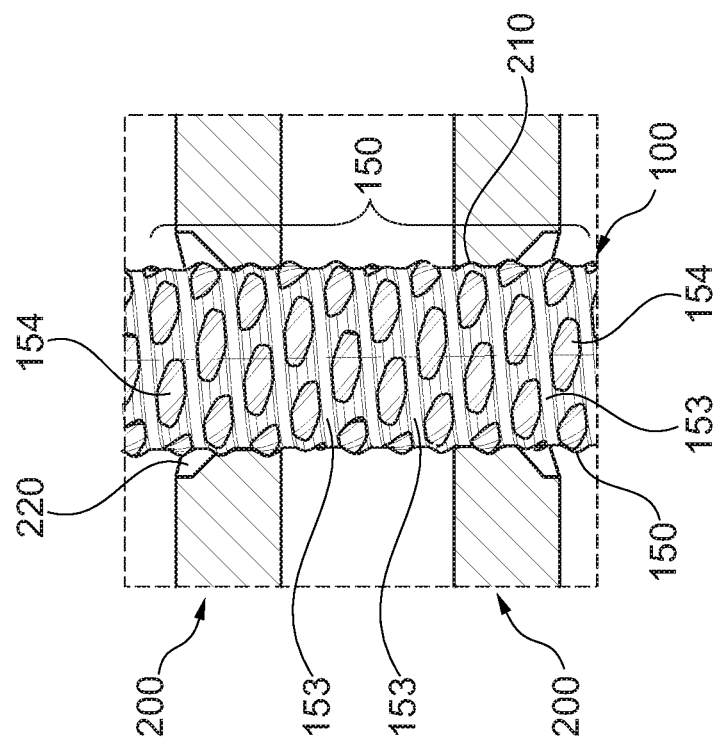
FIG. 4a and FIG. 4b are side cross-sectional views of an orthopedic locking system according to an embodiment of the present invention.
Figure 4A:
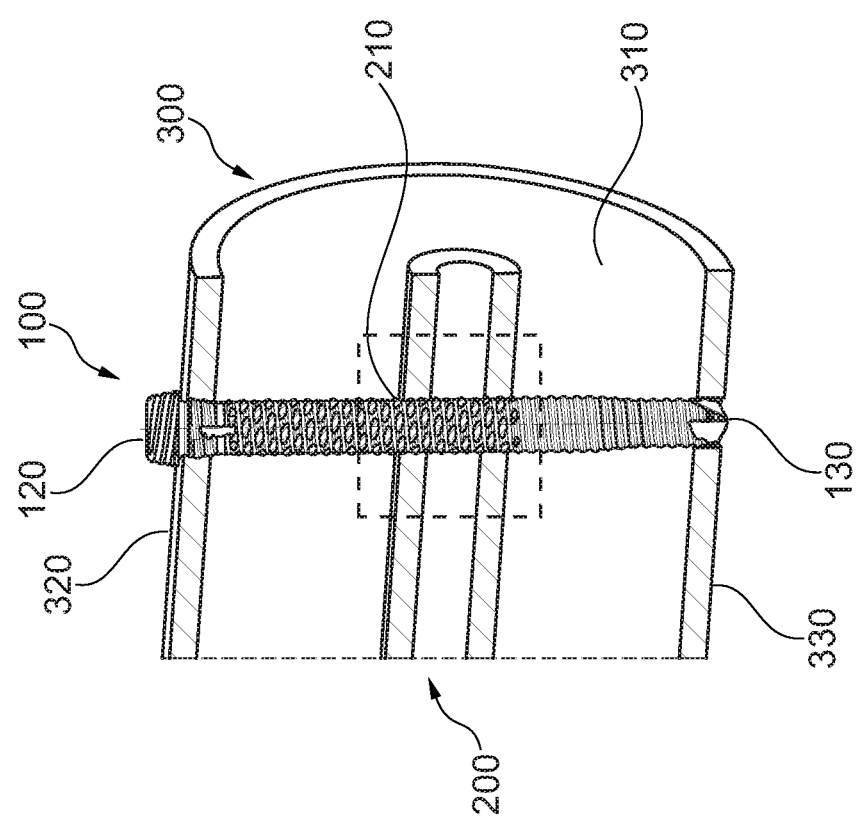
Figure 4C:
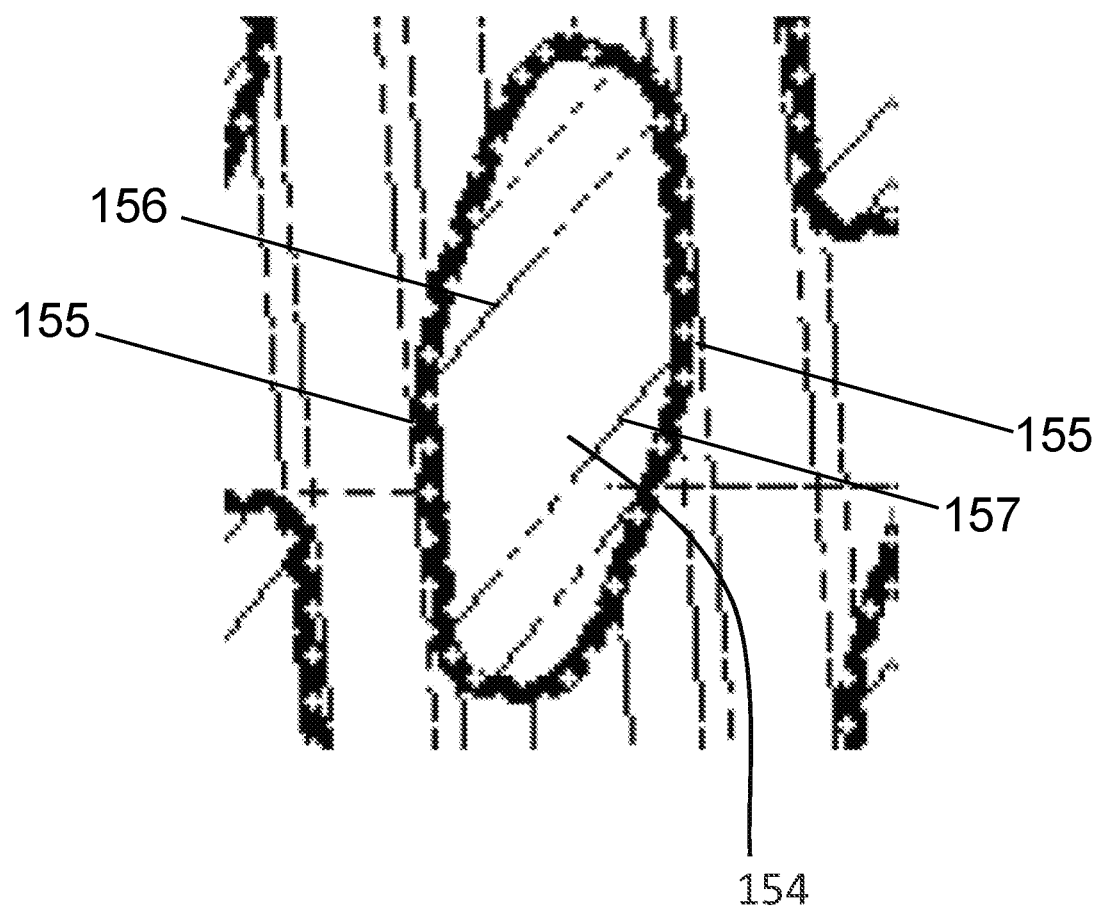
FIG. 4c is a close up side view of a shaft of the orthopedic locking screw of FIGS. 4a and 4b.

FIG. 4a and FIG. 4b show an orthopedic locking system using an orthopedic locking screw 100. An orthopedic implant 200 such as an intramedullary nail is inserted in a bone 300 comprising marrow 310. The marrow 310 is circumferentially encased by cortex as illustrated by a first cortex portion 320 and a second cortex portion 330. In a further step, a tip 130 of the locking screw 100 is inserted through the first cortex portion 320 and marrow 310 into a bore 210 of the orthopedic implant 200. A shaft 110 is advanced into the bore 210 in any sufficient manner, such that the tip 130 is advanced through the bore 210. Since the major diameter of the tip 130 is different (e.g., smaller) from the major diameter of a thread pattern section 150, the tip 130 operates to advance (e.g., by pushing) the shaft 110 forward through the bore 210 of the orthopedic implant 200. When the thread pattern section 150 comes into engagement with an internal thread 220 of the bore 210, the shaft 110 may be rotated, for example with a screw driver engaged at a screw head to advance the shaft 110 into and/or through the bore 210. Accordingly, the thread pattern section 150 engages the bore 210 so as to form a mechanical intermeshing fit with the internal thread 220 of the bore 210 as shown in FIG. 4a and FIG. 4b. When the tip 130 comes into contact with the bone 300 on the opposite side of the orthopedic implant 200, i.e., with the second cortex portion 330, the locking screw 100 is rotated further, so as to engage the tip 130 with the bone 300.

In case of a breakage of the locking screw 100 inside the bone 300, a proximal portion of the broken locking screw 100 may be removed by screwing out the screw 100 in the loosening direction using, for example, an appropriate screw driver. Further, a distal portion of the broken screw 100 may be removed by striking it at the broken side of the screw 100 in direction of the second cortex portion 330. The thread pattern section 150 generally cooperates with the internal thread 220 of the orthopedic implant 200 in an engaged state. However, the thread pattern section 150 also allows for overriding of the functional thread turns 151 and instead use of the left hand thread 152 in order to remove the broken screw 100 out of the implant 200. Hence, the broken locking screw 100 can be easily removed without injuring an adjacent bone tissue.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to a further advantage. Any reference signs in the claims should not be construed as limiting the scope.

The invention claimed is:

1. An orthopedic locking screw comprising:
a shaft including a thread pattern section extending along at least part of the shaft,
the thread pattern section including a first thread oriented in a first direction and a second thread oriented in a second direction opposite the first direction, the first thread including a helically extending crest and the second thread including a plurality of rhombic shaped crests recessed relative to the helically extending crest,
wherein a minimum height of each rhombic shaped crest of the plurality of rhombic shaped crests is raised relative to a first surface of the shaft, and
wherein each rhombic shaped crest of the plurality of rhombic shaped crests includes a second surface at a first radius from a longitudinal axis of the shaft, the second surface having a perimeter defined in part by an edge extending across a width of the first thread, the edge being at an oblique angle relative to an alignment direction of the helically extending crest adjacent to the rhombic shaped crest.

2. The orthopedic locking screw of claim 1, wherein the plurality of rhombic shaped crests together define a helical path along part of the shaft.

3. The orthopedic locking screw of claim 2, wherein the plurality of rhombic shaped crests include at least a first rhombic shaped crest smaller than a second rhombic shaped crest, the first rhombic shaped crest being closer to a tip of the shaft than the second rhombic shaped crest.

4. The orthopedic locking screw of claim 1, wherein the helically extending crest and each of the plurality of rhombic shaped crests have a first width measured in a direction perpendicular to a longitudinal axis of the first thread.

5. The orthopedic locking screw of claim 1, wherein the thread pattern section includes a helically extending root adjacent to the helically extending crest, the helically extending root being separated from each of the plurality of rhombic shaped crests by a step.

6. The orthopedic locking screw of claim 5, wherein the helically extending root does not overlap with the first thread or the second thread.

7. The orthopedic locking screw of claim 1, further comprising a head abutting an end of the shaft, the head having an outer thread oriented in the same direction as the second thread.

8. A system comprising:
the orthopedic locking screw of claim 1; and
an orthopedic implant including a bore with a threaded surface,
wherein the first thread of the orthopedic locking screw is functionally engageable with the threaded surface of the bore.

9. An orthopedic locking screw comprising:
a shaft including a thread pattern section over at least part of the shaft,
the thread pattern section including a helical crest and a helical root, a first part of the helical crest defining a first thread in a first direction and a second part of the helical crest defining a second thread in a second direction opposite the first direction, the first part being separate from the second part,
wherein the helical crest has a first minimum height relative to the helical root at the first part and a second minimum height relative to the helical root at the second part, the first minimum height being greater than the second minimum height, and the second minimum height being greater than zero, and
wherein the second part includes a plurality of second subparts, each of the plurality of second subparts including a circumferentially planar surface, a first tapered surface and a second tapered surface, the circumferentially planar surface-extending from a leading edge to a trailing edge, the leading edge and the trailing edge both being at an oblique angle relative to a longitudinal axis of the helical crest, the first tapered surface being in between the first part of the helical crest and the leading edge along the longitudinal axis, and the second tapered surface being in between the trailing edge and the first part of the helical crest along the longitudinal axis.

10. The orthopedic locking screw of claim 9, wherein the first part includes a plurality of first subparts, each of the plurality of first subparts being separated by one second subpart of the plurality of second subparts.

11. The orthopedic locking screw of claim 10, wherein each of the plurality of second subparts has a rhombic shape and each of the plurality of first subparts has a non-rhombic shape.

12. The orthopedic locking screw of claim 10, wherein a shape of the first tapered surface on a first side of a centerline of the helical crest is different from a shape of the second tapered surface on the first side.

13. The orthopedic locking screw of claim 9, wherein the second thread defines a helical path in the second direction such that each of the plurality of second subparts is separated by the helical root.

14. A system comprising:
the orthopedic locking screw of claim 9; and
an orthopedic implant including a bore with a threaded surface,
wherein the first thread of the orthopedic locking screw is functionally engageable with the threaded surface of the bore.

15. An orthopedic locking screw comprising:
a shaft including a thread pattern section over at least part of the shaft,
the thread pattern section including a first thread in a first direction and a second thread in a second direction opposite the first direction, the second thread being entirely within the first thread such that the second thread is defined by a plurality of recessed portions in the first thread,
wherein the first thread includes a crest centered along a first central longitudinal axis of the first thread extending helically about the shaft,
wherein each of the plurality of recessed portions includes a first edge, a second edge and a surface therebetween, the first edge and the second edge being on opposite sides of the first central longitudinal axis of the first thread and the surface being at a substantially uniform distance from a second central longitudinal axis of the shaft from a leading edge of the surface to a trailing edge of the surface, and
wherein each of the plurality of recessed portions is asymmetrical about a plane substantially aligned with and passing through the first central longitudinal axis and the shaft.

16. The orthopedic locking screw of claim 15, wherein each of the plurality of recessed portions has a first surface area on a first side of the first central longitudinal axis and a second surface area on a second side of the first central longitudinal axis, the first surface area being equal to the second surface area.

17. The orthopedic locking screw of claim 15, wherein the first edge and the second edge are adjacent to a root of the thread pattern section.

18. The orthopedic locking screw of claim 15, wherein each of the plurality of recessed portions extend a first maximum distance on a first side of the first central longitudinal axis and the first maximum distance on a second side of the first central longitudinal axis.

19. The orthopedic locking screw of claim 15, wherein each of the plurality of recessed portions has a shape with an axis of symmetry passing therethrough, the axis of symmetry being at an angle relative to the plane.

20. A system comprising:
the orthopedic locking screw of claim 15; and
an orthopedic implant including a bore with a threaded surface,
wherein the first thread of the orthopedic locking screw is functionally engageable with the threaded surface of the bore.

* * * * *